United States Patent
Lorenz

(10) Patent No.: US 6,277,154 B1
(45) Date of Patent: Aug. 21, 2001

(54) PRE-EMULSION AND USE THEREOF FOR THE PREPARATION OF A HAIR DYEING COMPOSITION AS WELL AS PROCESS FOR THE PREPARATION OF A HAIR DYEING EMULSION

(75) Inventor: Heribert Lorenz, Gross-Bieberau (DE)

(73) Assignee: Goldwell GmbH (DE)

( * ) Notice: Subject to any disclaimer, the term of this patent is extended or adjusted under 35 U.S.C. 154(b) by 0 days.

(21) Appl. No.: 09/498,662

(22) Filed: Feb. 7, 2000

(30) Foreign Application Priority Data

Feb. 11, 1999 (DE) .............................. 199 05 768

(51) Int. Cl.⁷ ...................................... A61K 7/13
(52) U.S. Cl. .............. 8/405; 8/636; 424/70.31; 510/421; 510/437; 510/491
(58) Field of Search .............. 424/70.31, 70.28; 510/421, 437, 491; 8/590, 408, 405, 636

(56) References Cited

U.S. PATENT DOCUMENTS

| | | | |
|---|---|---|---|
| 5,525,123 | * | 6/1996 | Lorenz et al. ............................ 8/408 |
| 5,642,480 | * | 6/1997 | Vermeer et al. .................. 424/70.24 |
| 6,136,884 | * | 10/2000 | Chen et al. ............................ 523/105 |
| 6,190,678 | * | 2/2001 | Hasenoehri et al. ................. 424/401 |

FOREIGN PATENT DOCUMENTS

| | | | |
|---|---|---|---|
| 19701422 | * | 5/1998 | (DE) . |
| 4017718 | * | 5/1998 | (DE) . |
| 19807508 | * | 4/1999 | (DE) . |
| 2129447 | * | 5/1984 | (GB) . |

* cited by examiner

*Primary Examiner*—Lorna M. Douyon
*Assistant Examiner*—Anil K. Puri
(74) *Attorney, Agent, or Firm*—Norris, McLaughlin & Marcus P.A.

(57) ABSTRACT

The invention concerns a pre-emulsion for the simple preparation of a hair dyeing composition, comprising a combination of a) 20% to 40% by weight of at least one $C_{12}$–$C_{14}$-fatty alcohol ethoxylate with 1 to 5 ethylene oxide groups;

b) 15% to 40% by weight of oleic acid;

c) 10% to 30% by weight of ethanediol and/or 1.2-propanediol distearate;

d) 5% to 20% by weight of glyceryl stearate and/or at least one sugar fatty acid ester; and, e) 0% to 25% by weight of at least one $C_{12}$–$C_{18}$-fatty alcohol, each calculated to the total pre-emulsion composition; containing no further emulsifiers or fatty substances, having a maximum water content of 10% by weight, in particular 5% by weight, whereby the pH-value is preferably between 7.1 and 9.

This pre-emulsion can be mixed at a low temperature with a customary aqueous composition, comprising at least one oxidation dyestuff precursor, to give a stable hair dyeing emulsion.

7 Claims, No Drawings

PRE-EMULSION AND USE THEREOF FOR THE PREPARATION OF A HAIR DYEING COMPOSITION AS WELL AS PROCESS FOR THE PREPARATION OF A HAIR DYEING EMULSION

BACKGROUND OF THE INVENTION

The present invention concerns a pre-emulsion and a process for the preparation of a composition for the dyeing of human hair on the basis of a fine, aqueous emulsion, comprising at least one oxidation dyestuff precursor.

SUMMARY OF THE INVENTION

Compositions for the permanent dyeing of human hair on the basis of oxidation dyestuff precursors are widely used. In general, they are applied by mixing a composition, usually an aqueous emulsion, comprising at least one oxidation dyestuff precursor, generally at least one developing and at least one coupling substance, shortly before application with a composition comprising a peroxide, the mixture then being brought onto the hair.

The invention therefore starts from the task of providing a more simple process for the preparation of hair dyeing emulsions which saves time and energy, whereby the obtained emulsions also ensure good mixability with the oxidation agent composition, i.e. generally with aqueous hydrogen peroxide, which, in turn, leads to even distribution of the ready-to-use hair dyeing composition on the hair and thereby to good coloration results.

According to the invention, this problem is solved by a process for the preparation of a hair dyeing emulsion, whereby a pre-emulsion of defined emulsifiers and fats is mixed at a maximum temperature of 60° C., in particular about 30° to about 50° C., with an aqueous composition comprising at least one oxidation dyestuff precursor.

BRIEF DESCRIPTION OF THE PREFERRED EMBODIMENT

The preferred weight proportion between pre-emulsion and aqueous composition ranges from about 15 to 40 and 85 to 60, in particular about 1 to 2.

This pre-emulsion comprises:

a) 20% to 40% by weight of at least one $C_{12}$–$C_{14}$-fatty alcohol ethoxylate with 1 to 5 ethylene oxide groups;

b) 15% to 40% by weight of oleic acid;

c) 10% to 30% by weight of ethanediol and/or 1.2-propanediol distearate;

d) 5% to 20% by weight of glyceryl stearate and/or at least one sugar fatty acid ester; and, e) 0% to 25% by weight of at least one $C_{12}$–$C_{18}$-fatty alcohol, each calculated to the total pre-emulsion composition; containing no further emulsifiers or fatty substances, and having a maximum water content of 10% by weight, in particular 5% by weight, whereby the pH-value is preferably adjusted between 7.1 and 9 by ammonia and/or ethanolamine(s).

Used as component a) are preferably about 25% to 35% by weight of $C_{12}$–$C_{14}$-fatty alcohol ethoxylate, in particular Laureth-2 or Myristeth-3.

The oleic acid is also preferably contained in the pre-emulsion in an amount from about 25% to 35% by weight.

Preferred as component c) is ethanediol distearate, in particular in an amount from 15% to 25% by weight.

Used as component d) are in particular 5% to 15% by weight of glyceryl stearate, saccharose and glucose esters, such as glucose and methyl glucose dioleate, methyl glucose sesquistearate and/or polyglyceryl-3-methyl glucose distearate.

To the extent that a $C_{12}$–$C_{18}$-fatty alcohol is present as component e), this is preferably lauryl, myristyl, cetyl and coco fatty alcohol, preferably in an amount from 5% to 20% by weight.

By the use of this simple composition as pre-emulsion for the preparation of hair dyeing compositions, it is possible to prepare all required shades by admixture thereof with aqueous hair dyeing solutions and at low temperatures and thus economical energy consumption.

Preparation of the pre-emulsion is effected by mixing the molten components with a small proportion of water, i.e. a maximum of 10%, preferably not more than 5%, in particular less than about 3% by weight, which can be added, for example, as 25% ammonia solution to adjust the pH-value at 7.1 to 9, in particular about 7.5 to 8.5. Adjustment of the pH-value can also be effected by an ethanolamine, in particular monoethanolamine.

The viscosity of the pre-emulsion according to the invention preferably ranges from about 5,000 to 30,000, in particular from about 10,000 to 25,000, for example, from about 15,000 to 20,000 mPa•s, measured at 20° C. in a Brookfield Viscosimeter BVT.

The water phase of the ready-to-use finished product containing oxidation dyestuff precursors can comprise water-soluble emulsifiers. Useful as such are in particular anionic surfactants. Suitable anionic surfactants are present in particular in an amount from about 0.25% to 5% by weight, preferably about 0.4% to 2.5% by weight, calculated to the total composition (of the ready-to-use emulsion). These are anionic surfactants of the sulfate, sulfonate, carboxylate and alkyl phosphate type, especially, of course, those customarily used in hair treatment compositions, in particular, the known $C_{10}$–$C_{18}$-alkyl sulfates, and the respective ether sulfates, for example, $C_{12}$–$C_{14}$-alkyl ether sulfate, lauryl ether sulfate, especially with 1 to 4 ethylene oxide groups in the molecule, acyl aminocarboxylic acids, such as lauroyl sarcosinate and glutamate, furthermore monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents. Additional anionic surfactants useful within the scope of the invention are α-olefin sulfonates or the salts thereof, and alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

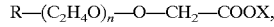

$$R\text{—}(C_2H_4O)_n\text{—}O\text{—}CH_2\text{—}COOX,$$

wherein R is a $C_8$–$C_{20}$-alkyl group, preferably a $C_{12}$–$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids.

Such products have been known for some time and are on the market, for example, under the trade name "AKYPO®" and "AKYPO-SOFT®". Also useful are $C_8$–$C_{20}$-acyl isethionates, alone or in admixture with other surfactants, and sulfofatty acids and the esters thereof.

It is optionally also possible to use amphoteric or zwitterionic surfactants as water-soluble emulsifiers, in particular in admixture with anionic surfactants, whereby the total amount should preferably range from about 0.25% to 5%, in particular about 0.5% to 2.5% by weight, calculated to the total hair dyeing emulsion.

Useful as such are in particular the various known betaines such as fatty acid amido alkyl betaines and sulfobetaines, for example, lauryl hydroxy sulfobetaine; long-chain alkyl amino acids, such as cocoaminoacetate, cocoaminopropionate and sodium cocoamphopropionate and -acetate have also proven suitable.

Also useful are nonionic, water-soluble surfactants, for example, from $C_8$–$C_{18}$-alkyl polyglucosides with a polymerization degree of 1 to 5, in the named amounts alone or in admixture with anionic and/or amphoteric or zwitterionic surface-active substances. Amineoxides are also useful.

Further useful surfactants are also cationic surfactants, such as the known quaternary ammonium compounds with one or two alkyl or alkenyl groups with 10 to 22 carbon atoms in the molecule, in particular in an amount from 0.1% to 7.5%, preferably 0.25% to 5%, especially preferred 0.5% to 2.5% by weight, calculated to the total composition.

The hair dyeing emulsion prepared by use of the pre-emulsion prepared according to the invention comprises at least one oxidation dyestuff precursor; useful is a mixture of at least one developing and at least one coupling substance. These are known per se and described, for example, in the monography of K. Schrader, "Grundlagen und Rezepturen der Kosmetika", 2nd Ed. (1989), pp. 784–799.

Examples of developing substances are in particular 1.4-diaminobenzene, 2.5-diaminotoluene, tetraaminopyrimidines, triaminohydroxypyrimidines, 1.2.4-triaminobenzene, 2-(2.5-diamino-phenyl)ethanol, 2-(2'-hydroxyethyl amino)-5-aminotoluene and 1-amino-4-bis-(2'-hydroxyethyl)-aminobenzene, or the water-soluble salts thereof; examples for coupling substances are resorcinol, 2-methyl resorcinol, 4-chlororesorcinol, 2-amino-4-chlorophenol, 4-(N-methyl) aminophenol, 2-aminophenol, 3-aminophenol, 1-methyl-2-hydroxy-4-aminobenzene, 3-N,N-dimethyl aminophenol, 4-amino-3-methyl phenol, 5-amino-2-methyl phenol, 6-amino-3-methyl phenol, 3-amino-2-methyl amino-6-methoxypyridine, 2-amino-3-hydroxypyridine, 4-aminodiphenylamine, 4.4'-diaminodiphenylamine, 2-dimethyl amino-5-aminopyridine, 2.6-diaminopyridine, 1.3-diaminobenzene, 1-amino-3-(2'-hydroxyethyl amino)benzene, 1-amino-3-[bis (2'-hydroxyethyl) amino]benzene, 1.3-diaminotoluene, α-naphthol, 1.4-diamino-2-chlorobenzene, 4.6-dichlororesorcinol, 4-hydroxy-1.2-methylene dioxybenzene, 1.5-dihydroxynaphthaline, 1.7-dihydroxynaphthaline, 2.7-dihydroxynaphthaline, 1-hydroxynaphthaline, 4-hydroxy-1.2-methylene dioxybenzene, 2.4-diamino-3-chlorophenol, and/or 1-methoxy-2-amino-4-(2'-hydroxyethyl amino) benzene, whereby this list is just exemplary.

Developing and coupling substances are preferably contained in a molar proportion of 1:3 to 5:1, in particular about 1:1 and about 3:1; their proportion in the hair dyeing emulsions according to the invention may range from about 0.1% to about 5% by weight, depending on the desired coloration.

It is useful to incorporate these oxidation dyestuff precursors already into the aqueous phase; however, if desired, they can also be added to the finished emulsion.

Optionally, the hair dyeing compositions prepared according to the invention can also comprise so-called shading agents for the fine-tuning of the desired shade, in particular also direct-acting dyestuffs.

Such shading agents are, for example, nitro dyestuffs, such as 2-amino-4.6-dinitrophenol, 2-amino-4-nitrophenol, 2-amino-6-chloro-4-nitrophenol, etc., preferably in amounts ranging from about 0.05% to 2.5%, in particular 0.1% to 1% by weight, calculated to the dyeing composition (excluding the oxidation composition).

The hair dyeing composition emulsions prepared according to the invention can comprise basic substances and additives customarily found in such compositions, conditioning agents, stabilizers, fats and oils, thickening agents, complexing agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815.

The hair dyeing emulsions prepared according to the invention preferably have a pH-value in the alkaline range, in particular between about 8 and about 12.5, preferably between 8.5 and 11.

For application, the oxidation dyestuff precursor emulsion prepared according to the invention is mixed with an oxidation agent composition. The preferred oxidation agent is hydrogen peroxide, for example, in concentrations between 2% to 6%.

However, it is also possible to use other peroxides, such as urea peroxide and melamine peroxide.

The pH-value of the ready-to-use hair dyeing composition, i.e. after admixture with peroxide, may be in the slightly acidic range, i.e. between 5.5 to 6.9, as well as in the neutral range and in the alkaline range, i.e. between pH 7.1 and 10.

Following are Examples which illustrate the invention.

EXAMPLE 1

A mixture of 12 kg Laureth-2, 10 kg oleic acid, 7 kg ethanoldiol distearate, and 3 kg glyceryl stearate was melted together under stirring at about 55° C. and subsequently emulsified with 1 kg water, whereby a pH-value of 8.5 was adjusted with ammonia.

The pasty, pumpable pre-emulsion thus obtained can easily be mixed at room temperature with an aqueous composition composed of

| | |
|---|---|
| 2.5-Diaminotoluene sulfate | 0.75 (% by wt.) |
| Resorcinol | 0.28 |
| 3-Aminophenol | 0.03 |
| 4-Amino-3-methylphenol | 0.03 |
| 2-Amino-3-hydroxypyridine | 0.05 |
| 2-Amino-4-hydroxyethyl aminoanisole | 0.03 |
| Sodium lauryl sulfate | 0.50 |
| Ammonium chloride | 0.25 |
| Sodium sulfite | 0.25 |
| Tetrasodium-EDTA | 0.20 |
| Ascorbic acid | 0.15 |
| Wheat protein hydrolyzate | 0.20 |
| Perfume | 0.20 |
| Ammonia | ad pH 10.00 |
| Water | ad 100.00 | in a weight proportion between fatty phase : water phase of 1 to 2, whereby a stable, aqueous emulsion is obtained.

Human hair was dyed for 25 minutes with a reaction product of this hair dyeing emulsion and an aqueous 6% hydrogen peroxide composition in a weight proportion of 1:1. After shampooing and drying, an intensive, light-stable, brown-violet coloration was obtained.

EXAMPLE 2

A mixture of 10 kg Coceth-3, 10 kg oleic acid 4 kg ethanediol-/1.2-Propanediol stearate (1:1), 4 kg cetyl alcohol, and 3.5 kg polyglyceryl-3-methyl glucose distearate was mixed at about 50° C. and subsequently emulsified with 1 kg water and the addition of monoethanol amine to adjust a pH-value of 8.0.

The stable, pumpable, pasty pre-emulsion was mixed at about 40° C. with an aqueous dyeing composition composed of:

| | |
|---|---|
| 2.5-Diaminotoluene sulfate | 1.00 (% by wt.) |
| 4-Amino-2-hydroxytoluene | 1.60 |
| 1-Naphthol | 0.40 |
| 2.5.6-Triamino-4-hydroxypyrimidine sulfate | 0.40 |
| Sodium lauryl sulfate | 1.00 |
| Sodium sulfite | 0.50 |
| Silica | 0.25 |
| Citric acid | 0.65 |
| Panthenol | 0.25 |
| Cationized plant protein hydrolyzate | 0.25 |
| Ascorbic acid | 0.20 |
| Perfume | 0.40 |
| Monoethanolamine | 9.80 |
| Water | ad 100.00 |

A stable hair dyeing emulsion was obtained.

Admixing in a weight proportion of 1 to 1 with a 6% hydrogen peroxide composition results in an intensive, light- and shampoo-stable violet coloration of human hair.

What is claimed is:

1. Pre-emulsion for the preparation of a hair dyeing composition, comprising a combination of
   a) 20% to 40% by weight of at least one $C_{12}$–$C_{14}$-fatty alcohol ethoxylate with 1 to 5 ethylene oxide groups;
   b) 15% to 40% by weight of oleic acid;
   c) 10% to 30% by weight of ethanediol and/or 1.2-propanediol distearate;
   d) 5% to 20% by weight of glyceryl stearate and/or at least one sugar fatty acid ester; and,
   e) 0% to 25% by weight of at least one $C_{12}$–$C_{18}$-fatty alcohol, each calculated to the total pre-emulsion composition; containing no further emulsifiers or fatty substances, having a maximum water content of 10% by weight, whereby the pH-value is between 7.1 and 9.

2. Pre-emulsion according to claim 1, comprising as component a) 25% to 35% by weight of a lauryl alcohol ethoxylate with 2 ethylene oxide groups.

3. Pre-emulsion according to claim 1, comprising 25% to 35% by weight of oleic acid.

4. Pre-emulsion according to claim 1, comprising 15% to 25% by weight of ethanediol distearate.

5. Pre-emulsion according to claim 1, comprising as sugar fatty acid ester 5% to 15% by weight of methyl glucose sesquistearate and/or polyglyceryl-3-methyl glucose distearate.

6. Pre-emulsion according to claim 1, comprising a maximum of 5% by weight of water.

7. Process for the preparation of an emulsion for the dyeing of human hair, wherein a pre-emulsion according to claim 1 is mixed at a maximum temperature of 60°C. with an aqueous composition, comprising at least one oxidation dyestuff precursor.

* * * * *